United States Patent
Syed et al.

[11] Patent Number: 5,824,295
[45] Date of Patent: Oct. 20, 1998

[54] COMPOSITION FOR DECREASING COMBING DAMAGE AND METHODS

[75] Inventors: Ali N. Syed, Orland Park; Kaleem Ahmad, Chicago, both of Ill.

[73] Assignee: Avlon Industries, Inc., Bedford Park, Ill.

[21] Appl. No.: 627,345

[22] Filed: Apr. 4, 1996

Related U.S. Application Data

[63] Continuation-in-part of Ser. No. 267,829, Jun. 29, 1994, abandoned.

[51] Int. Cl.⁶ .................. A61K 7/06; A61K 7/09
[52] U.S. Cl. ............... 424/70.4; 424/70.2; 424/70.16; 424/70.17
[58] Field of Search ................ 424/70.11, 70.1, 424/70.4, 70.2, 70.16, 70.17

[56] References Cited

U.S. PATENT DOCUMENTS

| | | | |
|---|---|---|---|
| Re. 28,808 | 5/1976 | Panzer et al. | 260/2 BP |
| 3,259,570 | 7/1966 | Priesing | 210/53 |
| 3,879,464 | 4/1975 | Kalopissis et al. | 260/584 C |
| 3,915,904 | 10/1975 | Tonkyn | 260/2 BP |
| 3,958,581 | 5/1976 | Abegg et al. | 132/7 |
| 3,981,312 | 9/1976 | Patel | 424/70 |
| 4,009,255 | 2/1977 | Kalopissis et al. | 424/70 |
| 4,009,256 | 2/1977 | Nowak, Jr. et al. | 424/70 |
| 4,018,729 | 4/1977 | Faucher et al. | 260/17 R |
| 4,189,468 | 2/1980 | Vanlerberghe et al. | 424/70 |
| 4,210,161 | 7/1980 | Wagman | 132/7 |
| 4,228,810 | 10/1980 | Moore et al. | 132/7 |
| 4,240,450 | 12/1980 | Grollier et al. | 132/7 |
| 4,289,752 | 9/1981 | Mahieu et al. | 424/47 |
| 4,303,085 | 12/1981 | de la Guardia et al. | 132/7 |
| 4,314,572 | 2/1982 | de la Guardia et al. | 132/7 |
| 4,362,528 | 12/1982 | Grollier et al. | 8/406 |
| 4,371,517 | 2/1983 | Vanlerberghe et al. | 424/70 |
| 4,416,297 | 11/1983 | Wolfram et al. | 132/7 |
| 4,438,095 | 3/1984 | Grollier et al. | 424/70 |
| 4,445,521 | 5/1984 | Grollier et al. | 132/7 |
| 4,488,564 | 12/1984 | Grollier et al. | 132/7 |
| 4,507,280 | 3/1985 | Pohl et al. | 424/70 |
| 4,555,246 | 11/1985 | Grollier et al. | 8/405 |
| 4,557,928 | 12/1985 | Glover | 424/70 |
| 4,572,220 | 2/1986 | Hsiung et al. | 132/7 |
| 4,579,131 | 4/1986 | Syed | 132/7 |
| 4,591,610 | 5/1986 | Grollier | 524/55 |

(List continued on next page.)

FOREIGN PATENT DOCUMENTS

| | | |
|---|---|---|
| 0372546 | 7/1989 | European Pat. Off. . |
| 0443741 | 2/1991 | European Pat. Off. . |
| 1168017 | 4/1964 | Germany . |
| 2948947 | 6/1980 | Germany . |
| 2063671 | 11/1979 | United Kingdom . |
| 2071495 | 3/1981 | United Kingdom . |
| 2098226 | 5/1982 | United Kingdom . |
| 2122898 | 7/1983 | United Kingdom . |

*Primary Examiner*—Sally Gardner-Lane
*Attorney, Agent, or Firm*—Gardner, Carton & Douglas

[57] ABSTRACT

A composition for treating hair includes at least one of the following:

a) a cationic polymer made from the reaction of secondary amines and epihalohydrin and further cross-linked with the addition of a small amount of ethylene diamine;

b) dimethylaminoethylmethacrylate and one of a precomponent of an active hair relaxing ingredient, guanidine hydroxide or a shampoo base;

c) polyquaternium 10 and at least one of an active hair relaxing ingredient and an active hair relaxing ingredient; and d) polyquaternium 32 and mineral oil.

A method of using at least one of a cationic polymer, dimethylaminoethylmethacrylate, polyquaternium 10 or polyquaternium 32 includes the steps of applying one of the above to hair that is in risk of damage from a cosmetic procedure and exposing the hair to a cosmetic procedure.

8 Claims, 3 Drawing Sheets

U.S. PATENT DOCUMENTS

| | | | |
|---|---|---|---|
| 4,602,648 | 7/1986 | Syed et al. | 132/7 |
| 4,605,018 | 8/1986 | de la Guardia et al. | 132/7 |
| 4,638,822 | 1/1987 | Grollier et al. | 132/7 |
| 4,661,259 | 4/1987 | Walterick, Jr. et al. | 210/666 |
| 4,663,158 | 5/1987 | Wolfram et al. | 424/70 |
| 4,695,653 | 9/1987 | Kalopissis et al. | 564/505 |
| 4,710,374 | 12/1987 | Grollier et al. | 424/61 |
| 4,719,104 | 1/1988 | Patel | 424/70 |
| 4,761,273 | 8/1988 | Grollier et al. | 424/47 |
| 4,770,040 | 9/1988 | Grollier | 424/70.17 |
| 4,842,851 | 6/1989 | Grollier et al. | 424/47 |
| 4,871,530 | 10/1989 | Grollier et al. | 424/70 |
| 4,913,900 | 4/1990 | Kolc et al. | 424/72 |
| 4,948,579 | 8/1990 | Jacquet | 424/70.17 |
| 4,950,485 | 8/1990 | Akhtar et al. | 424/71 |
| 4,976,956 | 12/1990 | Noe | 424/70 |
| 4,996,006 | 2/1991 | Constantine et al. | 252/550 |
| 4,996,059 | 2/1991 | Grollier et al. | 424/71 |
| 5,009,880 | 4/1991 | Grollier et al. | 424/47 |
| 5,057,311 | 10/1991 | Kamegai et al. | 424/70 |
| 5,059,414 | 10/1991 | Dallal et al. | 424/70 |
| 5,060,680 | 10/1991 | Akhtar | 132/204 |
| 5,068,101 | 11/1991 | Akhtar et al. | 424/71 |
| 5,077,042 | 12/1991 | Darkwa et al. | 424/71 |
| 5,089,252 | 2/1992 | Grollier et al. | 564/47 |
| 5,136,093 | 8/1992 | Smith | 564/197 |
| 5,139,037 | 8/1992 | Grollier et al. | 132/203 |
| 5,148,822 | 9/1992 | Akhtar | 132/204 |
| 5,194,260 | 3/1993 | Grollier et al. | 424/401 |
| 5,221,530 | 6/1993 | Janchitraponvej et al. | 424/70 |

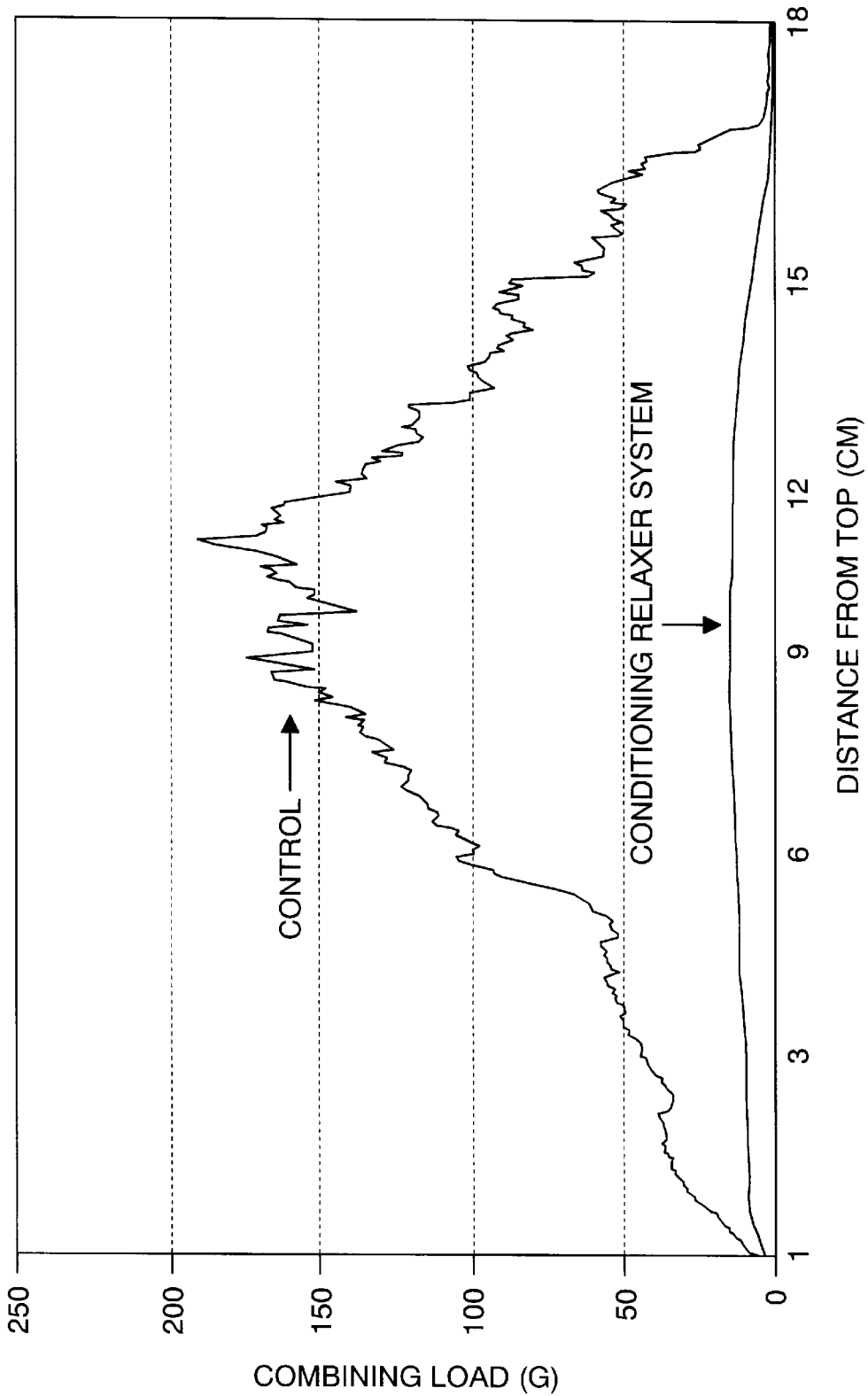

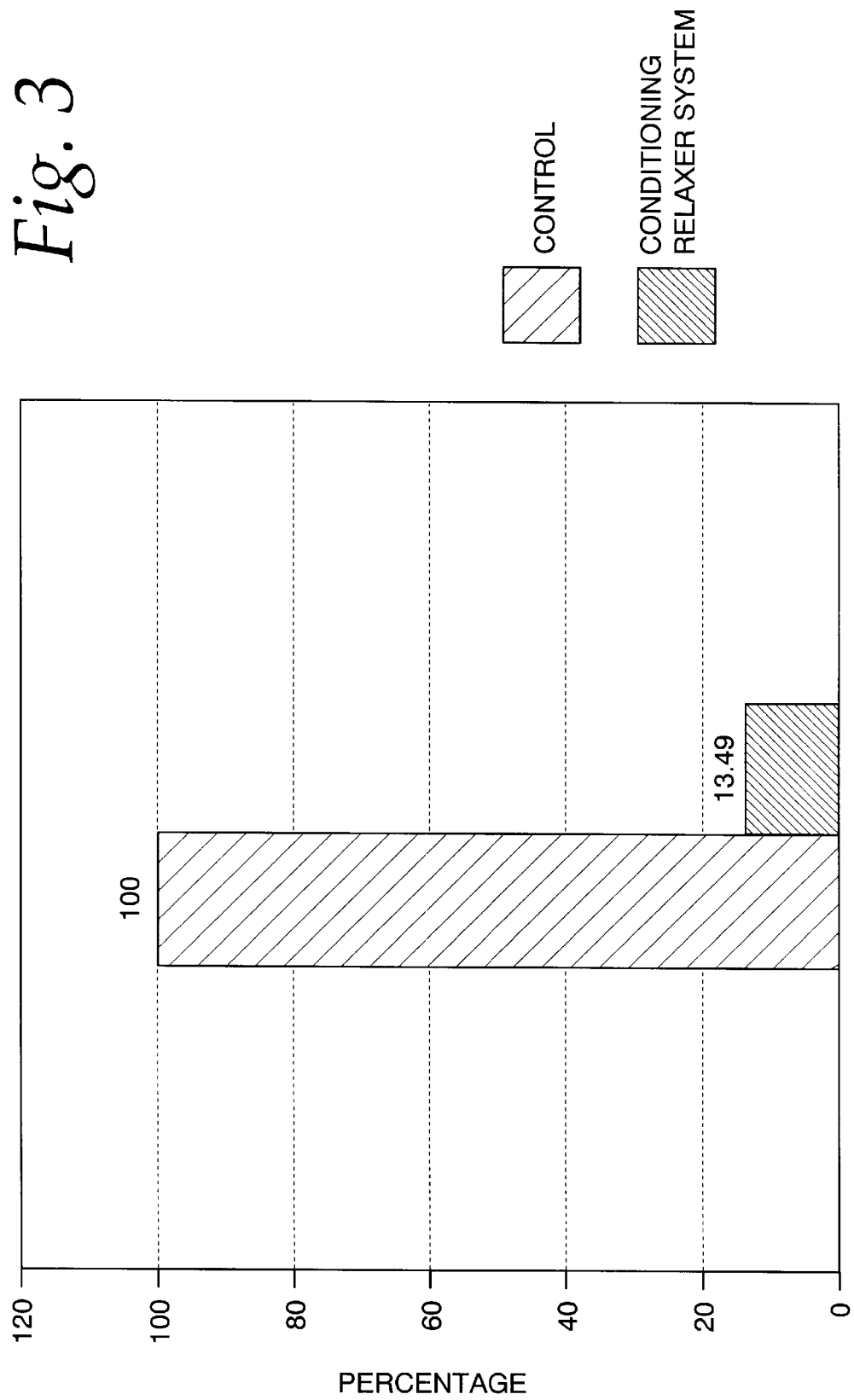

5,824,295

COMPOSITION FOR DECREASING COMBING DAMAGE AND METHODS

CROSS REFERENCES OF RELATED APPLICATIONS

This application is a continuation of our application Ser. No. 08/267,829, filed Jun. 29, 1994, now abandoned.

TECHNICAL FIELD

This invention generally relates to decreasing combing damage to hair. More particularly, the invention relates to a composition and method for decreasing damage caused by combing human hair exposed to a high alkalinity relaxer.

BACKGROUND OF THE INVENTION

Human hair has a variety of textures, from fine to coarse and from straight to very curly. Hair is made of keratin which in turn is made of polypeptide chains bonded together by cystine (or disulfide) bonds, hydrogen bonds and salt linkages. Hair undergoes various types of damage depending on the cosmetic procedure, e.g., relaxing, combing, shampooing, coloring, bleaching, weathering, perming and the like, to which it is subjected. The combing process is very damaging because of the high force levels involved and its repetitive nature and is especially damaging to hair that has been exposed to a high alkalinity relaxer. Wet hair is even more prone to combing damage as compared to dry hair because wet hair lacks the hydrogen bonding of dry hair and therefore is weaker.

Curly hair is made of hair strands that have irregular surfaces that mesh and tangle with each other to make combing more difficult. The diameter along the length of a curly hair strand is nonuniform which results in sections having a reduced diameter that are more prone to breakage during combing. In contrast, straight hair is made of hair strands whose surfaces are smooth and therefore do not mesh. Furthermore, the diameter along the straight hair strand is a generally uniform diameter. Straight hair thus lacks the reduced diameter sections of curly hair strands which makes straight hair strands less prone to breakage during combing.

Among individuals with excessively curly hair, e.g., individuals of African or Middle Eastern descent, it is especially popular to relax or straighten hair to increase hair manageability and ease of styling. The hair to be relaxed is exposed to a relaxer that chemically transforms cystine bonds of the hair to lanthionine bonds. For this reason, the chemical term for the hair relaxing process is lanthionization.

During relaxing, the hair is wetted with the relaxer and repeatedly smoothed and sometimes partially combed. Typical relaxers contain an alkali metal hydroxide or guanidine hydroxide as an active ingredient. As discussed above, wet hair is more prone to combing damage than dry hair. This is especially true during the relaxing process wherein the hair is also weakened by the chemical transformation.

Once the desired degree of straightening is achieved, the relaxer is rinsed from the hair with water. The hair is then cleansed using a non-detangling, low pH, acidic shampoo which is known as a neutralizing shampoo. After shampooing, the hair is very raspy in nature and rough to the touch. If the hair is combed after shampooing, there is a substantial amount of hair breakage along with discomfort to the scalp caused by the pulling required to untangle the hair.

Conditioners are often applied to the hair after shampooing to soften the hair. Quaternary ammonium compounds having chain lengths of about 12 to about 18 carbon atoms are often a component of these conditioners. Unfortunately, most of these compounds do not work when exposed to the relaxer or shampoo, and, therefore, they can only be used in post-shampooing conditioners. For example, U.S. Pat. Nos. 5,060,680 and 5,148,822, both to Akhtar, disclose straightening hair by a method that requires removing substantially all of the relaxer from the hair prior to applying an aqueous hair texturing and strengthening composition to the hair.

It is, therefore, an object of the present invention to provide an improved composition and easy-to-use method for decreasing combing damage to hair.

SUMMARY OF THE INVENTION

The present invention provides an improved composition and method for decreasing combing damage to hair. The composition and method are particularly useful for decreasing combing damage to human hair straightened by a high alkalinity relaxer.

According to the invention, a composition for treating hair includes a cationic polymer in an amount effective to decrease damage to the hair due to combing. One type of preferred cationic polymer is a water dispersible polyquaternary ammonium polymer that is the reaction product of a lower dialkylamine ($C_1$–$C_3$), a difunctional epoxy-type reactant and a third reactant selected from the group consisting of ammonia, primary amines, alkylene diamines having two to six carbon atoms and polyamines. Optionally, the composition can include a polyol, at least one precomponent of an active hair relaxing ingredient, an active hair relaxing ingredient or a shampoo base.

The method includes the steps of applying a cationic polymer to hair that is at risk of damage due to combing, thereby decreasing the damage to the hair when it is subsequently combed. The method can include the step of relaxing the hair before or after applying the cationic polymer to the hair.

In another embodiment of the method, a cationic polymer containing relaxer is applied to the hair. In yet a further embodiment, the cationic polymer is combined with a shampoo base to produce a shampoo that is applied to the hair.

The present composition and method that include the cationic polymer decrease combing damage, even in the presence of the relaxer, without requiring application of the cationic polymer after substantially all of the relaxer has been removed from the hair.

The present invention is also directed to a dimethylaminoethylmethacrylate containing multi-part relaxer and shampoo and a method of using dimethylaminoethylmethacrylate in the multi-part relaxer and the shampoo. The dimethylaminoethylmethacrylate decreases combing damage to hair, especially hair that has been exposed to a relaxer.

In still another embodiment, the present invention is directed to a polyquaternium 10 containing relaxer and method of using polyquaternium 10 in a relaxer. The polyquaternium 10 decreases the combing damage to hair, especially hair that has been exposed to a relaxer.

In yet another embodiment, the present invention is directed to a method of using polyquaternium 32 (a dimethlyaminoethlymethacrylate/acrylamide copolymer) dispersed in mineral oil to treat hair and a composition containing the same for treating hair. The method includes the steps of applying the neat dispersion to hair that is at risk of damage due to combing and decreasing the damage. The polyquaternium 32 and mineral oil dispersion decreases the combing damage to the hair.

BRIEF DESCRIPTION OF THE DRAWINGS

FIG. 2 is a graph comparing combing load (i.e., the force necessary to pull the comb through the hair) versus the distance from the top of a hair tress for a control hair tress and a hair tress treated with a conditioning relaxer system including compositions of the present invention.

FIG. 3 is a bar graph comparing the percent work required to comb a control hair tress versus a hair tress treated with the conditioning relaxer system.

DETAILED DESCRIPTION OF THE PREFERRED EMBODIMENTS

Figure 1:
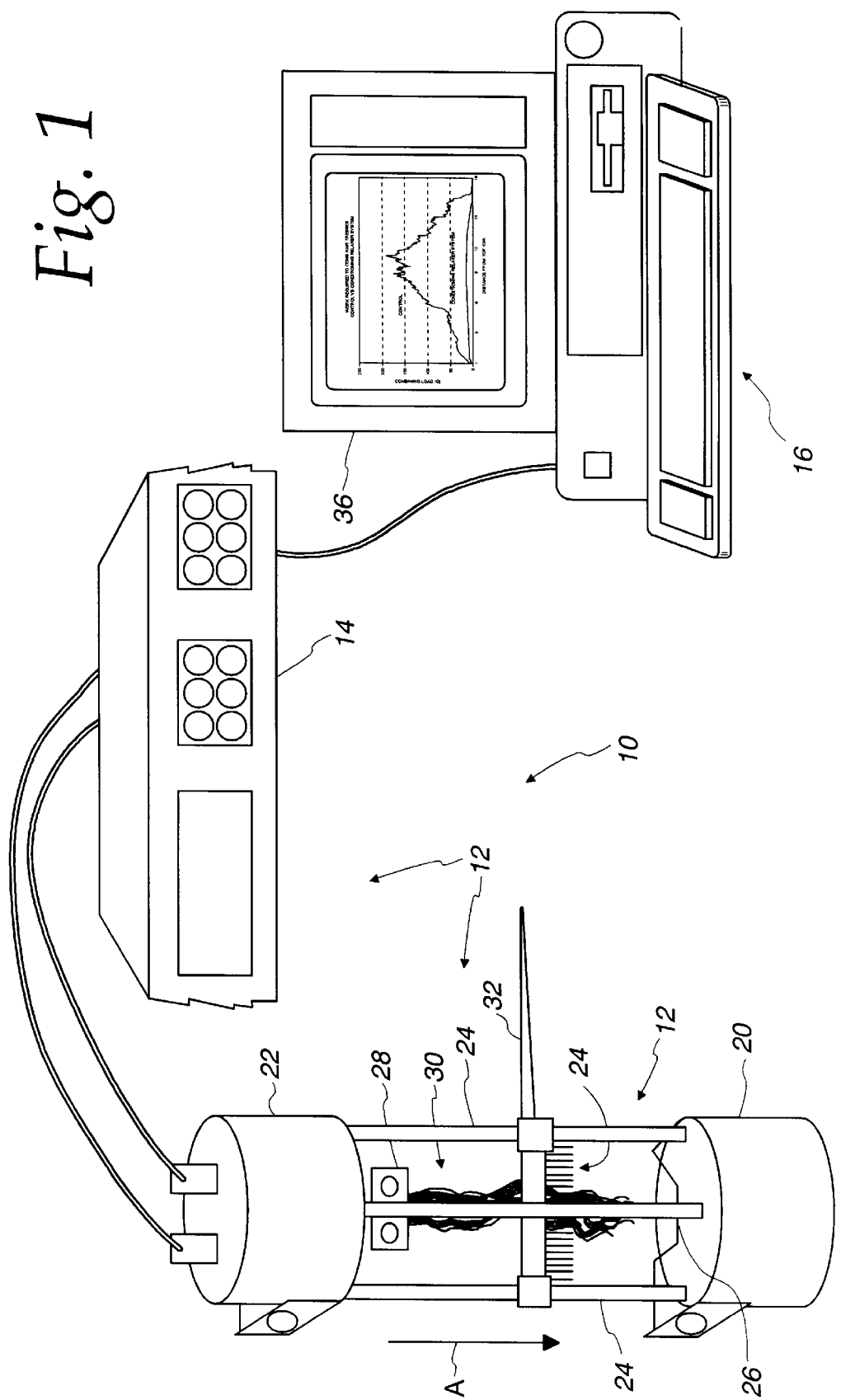
FIG. 1 illustrates a Dia-Stron MTT testing device.

A composition for treating hair includes a cationic polymer in an amount effective to decrease damage to the hair due to combing. The hair is preferable human hair although the composition can be used on other types of animal hair. The molecular weight of the cationic polymer is in the range of about $400 \times 10^3$ to about $1 \times 10^6$.

One type of preferred cationic polymer is described in more detail in U.S. Pat. No. Re. 28,808 to Panzer et al and U.S. Pat. No. 4,661,259 to Walterick et al. and is referred to in the '259 patent as the group (II) cationic polymer at column 3, lines 43 et seq. This cationic polymer is a water-dispersible polyquaternary polymer that is the reaction product of a lower dialkylamine ($C_1$–$C_3$), a difunctional epoxy-type reactant and a third reactant selected from the group consisting of ammonia, primary amines, dialkylenediamines having two to six carbon atoms and polyamines.

Representative epoxy-type reactants include epihalohydrins, e.g., epichlorohydrin and epibromohydrin with epichlorohydrin being the preferred epihalohydrin, diepoxides, e.g., 1,4-butanediol-diglycidyl ethers, and precursors of epihalohydrins and diepoxides, e.g., 1,3-dichloropropanol-2 and 1,4-dichloro-2,3-dihydroxybutane.

Representative polyamines include polyalkylpolyamines having the structure disclosed in the '259 patent at column 3, lines 64 et seq.

The exact reaction parameters for this preferred cationic polymer are specified in the '808 reissue patent and need not be repeated herein.

More specifically, this preferred cationic polymer is the reaction product of a secondary amine and epihalohydrin in the presence of a small amount of ethylenediamine. See, for instance, EXAMPLE 2 of the '808 reissue patent.

It is presently theorized that this preferred cationic polymer has the following structure:

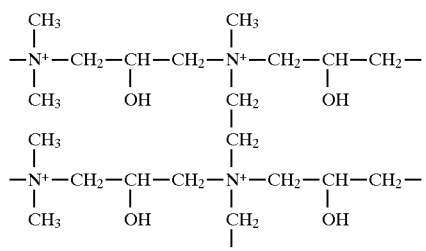

The molecular weight of this preferred cationic polymer is in the range of about $400$–$600 \times 10^3$.

This preferred cationic polymer in admixture with water is commercially available from BETZ® Laboratories, Trevose, Pa. under the designation BETZ® polymer 1195.

The BETZ® polymer 1195 typically contains about 50 weight percent (wt %) of the cationic polymer and has an activity of about fifty percent.

Although the composition can be used to decrease combing damage to hair exposed to cosmetic procedures such as coloring, bleaching, weathering, perming and the like, it is particularly useful on hair exposed to a high alkalinity relaxer to relax or straighten the hair.

The composition can be a conditioning composition in neat form, i.e., only the cationic polymer or the cationic polymer admixed with water, or the conditioning composition can further include a polyol. The conditioning composition can be a pre- or post-conditioning composition, i.e., the conditioner can be applied prior to or after the cosmetic procedure. When the cosmetic procedure is a relaxing procedure, the conditioning composition can be present on the hair with the relaxer.

The polyol is a low molecular weight polyol, i.e., preferably less than about 150 daltons, that facilitates the application of the cationic polymer. Representative polyols include glycerin and lower alkylene glycols having two to five carbon atoms in the alkyl group, e.g., ethylene glycol and propylene glycol.

When the conditioning composition includes the polyol, the cationic polymer is present in an amount in the range of about 1.0 to about 30 wt % and the polyol is present in an amount in the range of about 70 to about 99 wt %.

The composition can also be one part of a multi-part hair relaxer system or can be a single part hair relaxer. Multi-part relaxer systems having two parts are known wherein the active hair relaxing ingredient, e.g., guanidine hydroxide, is generated in situ by the combination of the two parts. Typically, the multi-part relaxer system includes a creme relaxer as part A and a liquid activator as part B. Preferably, the cationic polymer is a component of the creme relaxer. Also present in the creme relaxer is one precomponent of the active hair relaxing ingredient. A preferred precomponent is a hydroxide such as an alkaline earth hydroxide, e.g., calcium hydroxide. The liquid activator contains a second precomponent of the active hair relaxing ingredient, such as those disclosed in U.S. Pat. No. 4,314,572 to de la Guardia. A preferred second precomponent is guanidine carbonate. When parts A and B are mixed together, the calcium hydroxide and the guanidine carbonate react to produce guanidine hydroxide, the active hair relaxing ingredient. The creme relaxer, Part A, may also include additional conventional components. The liquid activator, Part B, typically also includes deionized water.

Preferably, the cationic polymer is present in the creme relaxer in an amount in the range of about 0.5 to about 5.0 wt %, based on the total weight of the creme relaxer.

The single part hair relaxer preferably uses a hydroxide such as an alkali metal hydroxide, e.g., sodium hydroxide, as the active hair relaxing ingredient. The remaining components of the single part hair relaxer are conventional.

The cationic polymer is present in the single part relaxer in an amount in the range of about 0.5 to about 5.0 wt %, based on the total weight of the single part relaxer.

The composition can also be a shampoo in general and a shampoo for neutralizing a high alkalinity hair relaxer in particular. The cationic polymer can be mixed with a conventional shampoo base to produce the shampoo. A preferred shampoo base is a neutralizing shampoo base for treating hair that has been exposed to a hair relaxer. The components, other than the cationic polymer, of the shampoo are conventional components of shampoos.

The cationic polymer is present in the shampoo in an amount in the range of about 0.5 to about 5.0 wt %, based upon the total weight of the shampoo.

The composition can be the cationic polymer neat, i.e., without any additional components other than water, provided the amount of cationic polymer used on the hair is effective to decrease damage to hair due to combing.

The composition can be applied to the hair to be treated before, during or after the hair is exposed to a procedure such as relaxing, coloring, bleaching, weathering, perming or the like, but preferably prior to combing.

In the method of using the cationic polymer to decrease damage to hair, the cationic polymer is applied to hair that is at risk of damage due to combing and the combing damage is decreased.

The method can also include the step of relaxing the hair with the relaxing step being performed after, before or simultaneously with the cationic polymer applying step.

The method can further include the steps of applying a high alkalinity relaxer to the hair and removing the relaxer from the hair. Preferably, the cationic polymer applying step is only performed before the relaxer removing step and is not performed thereafter. Alternatively, the cationic polymer applying step is performed after the relaxer removing step, before the relaxer applying step or simultaneously with the relaxer applying step.

The present invention is also directed to a dimethylaminoethylmethacrylate, a highly charged cationic polymer that preferably is a homopolymer, containing multipart relaxer system. The multi-part relaxer system is described above. A representative dimethylaminoethylmethacrylate cationic polymer is commercially available from Allied Colloid, Suffolk, Va. under the trade designation Salcare SC95, which is an admixture of dimethylaminoethylmethacrylate, mineral oil and PPG-1 trideceth-6. The dimethylaminoethylmethacrylate is also known as polyquaterium 37.

Preferably, the dimethylaminoethylmethacrylate is present in the cream relaxer in an amount in the range of about 0.5 to about 3 wt %, based on the total weight of the cream relaxer.

The present invention is also directed to a dimethylaminoethylmethacrylate containing shampoo which is an admixture of dimethylaminoethylmethacrylate and a shampoo base as described above.

The dimethylaminoethylmethacrylate is present in the shampoo in an amount in the range of about 0.5 to about 3 wt %, based upon the total weight of the shampoo.

In a method of using dimethylaminoethylmethacrylate to decrease damage to hair, the dimethylaminoethylmethacrylate is applied to hair that is at risk of damage due to combing, and the combing damage is decreased. The dimethylaminoethylmethacrylate can be applied in a relaxer or shampoo containing the same.

The present invention is also directed to a polyquaternium 10 containing relaxer. This relaxer can be either a multi-part relaxer or a single part relaxer, both of which are discussed above. A commercially available polyquaternium 10 cationic polymer is polymer JR-30M, from Amerchol Corporation, Edison, N.J.

The polyquaternium 10 is present in the creme relaxer of the multi-part relaxer in an amount in the range of about 0.5 to about 2 wt %, based on the total weight of the creme relaxer, and preferably in an amount in the range of about 0.5 to about 2 wt %, based on the total weight of the multi-part relaxer. The polyquaternium 10 is present in the single part relaxer in an amount in the range of about 0.5 to about 2 wt %, based upon the total weight of the single part relaxer.

In the method of using the polyquaternium 10 to decrease hair damage, the polyquaternium 10 is applied to hair that is at risk of damage due to combing, and the combing damage is decreased. The polyquaternium 10 is applied with the relaxing active ingredient.

The present invention also involves a method of using polyquaternium 32 cationic polymer dispersed in mineral oil to decrease combing damage to hair and a hair treating composition containing the same. Polyquaternium 32 dispersed in mineral oil is commercially available from Allied Colloid, Suffolk, Va. under the trade designation Salcare SC92. The method includes the preferred step of applying the neat dispersion to hair that is at risk of damage due to combing and decreasing the damage.

Tests were conducted to determine the efficacy of the cationic polymer, the dimethylaminoethylmethacrylate, the polyquaternium 10 and the polyquaternium 32 using a testing device 10 illustrated in FIG. 1 to determine the combing force exerted on the hair by a comb. Referring to FIG. 1, the testing device 10 includes a conventional Dia-Stron MTT equipped with a combing device 14 and a controller 16 that is interfaced with a personal computer 18. The combing device 14 includes a base 20 and an upper housing 22 interconnected by guides 24. A support 26 also extends between the base 20 and the upper housing 22. On the support 26 is a hair holder 28 adjacent to the upper housing 22. A tress of hair 30 is secured to and extends down from the hair holder 28 towards the base 20. A comb 32 extends between the guides 24 and has teeth 34 that engage the hair tress 30 as the comb 32 moves in the direction indicated by arrow A during testing.

If it is difficult for the teeth 34 to be pulled through the hair tress 30, the combing force on the hair is high, indicating that the hair tress 30 has many tangles. If it is easy for the teeth 34 to be pulled through the hair tress 30, the combing force on the hair is low, indicating that the hair tress 30 has little or no tangles. The combing forces are displayed on a monitor 36 of the computer 18. A combing force curve is transformed into work (in Joules) required to comb the hair. If the combing work required to comb the hair tress is high, the hair tress 30 was difficult to comb. If the combing work is low, the hair tress 30 is easy to comb.

The Dia-Stron MTT machine can apply up to 600 grams of force to a comb in order to pull that comb through a tress of hair. Initially, 2.0 grams of force were applied to the comb and in all cases (unless noted otherwise) the comb immediately and continuously moved through the hair at a speed of 120 mm per minute. The comb used was a bone rat tail having teeth 1.0 mm apart, made by American Comb, Patterson, N.J.

Each hair tress was tested five times by combing as follows:

First combing—initial detangling right after rinsing relaxer;

Second combing—a subsequent combing of the now detangled hair after spray wetting;

Third combing—initial detangling right after rinsing a non-detangling neutralizing shampoo from the hair;

Fourth combing—a subsequent combing of the now detangled hair after spray wetting; and Fifth combing—ease of dry combing.

The following examples are given by way of illustration and not limitation.

EXAMPLE I
BETZ® POLYMER 1195 PRECONDITIONER

A hair tress weighing 2.0 grains and 18 cm in length obtained from the DeMeo Brothers, New York, N.Y. was treated with 0.33 gm of neat cationic polymer, commercially available from BETZ® Industries under the trade designation BETZ® polymer 1195. The hair was from a Caucasian head. The tress was treated with 6 gm of Affirm® Sensitive Scalp Relaxer, commercially available from Avlon Industries, Inc., Chicago, Ill. for a time period of 18 minutes. Affirm® Relaxer contains guanidine hydroxide as the active ingredient. Then, the tress was rinsed with water and tested immediately after rinsing (first combing) and then spray-wetted and combed (second combing) using the above-described Dia-Stron MTT combing device. After testing, the tress was shampooed using one milliliter of a non-conditioning, non-detangling neutralizing shampoo, rinsed and tested immediately after rinsing (third combing) and then spray-wetted and combed (fourth combing) using the Dia-Stron MTT combing device. After drying, the hair tress was again tested (fifth combing).

The ease of wet combing was determined, and the area under the combing curve was calculated to determine the work done in Joules for each test. The test results are shown in TABLE 1, below.

TABLE 1

Pre-Relaxer Conditioner with Betz ® Polymer 1195

| PROPERTIES | CONTROL (JOULES) | 1195 PRECONDI- TIONER (JOULES) | % DECREASE IN COMBING WORK |
|---|---|---|---|
| 1ST COMBING: INITIAL DETANGLING RIGHT AFTER RINSING RELAXER | 0.11380 | 0.01261 | 88.92 |
| 2ND COMBING: EASE OF WET COMBING AFTER RINSING RELAXER | 0.09200 | 0.01017 | 88.95 |
| 3RD COMBING: INITIAL DETANGLING RIGHT AFTER RINSING NON-DETANGLING NEUTRALIZING SHAMPOO | 0.09300 | 0.00560 | 93.98 |
| 4TH COMBING: EASE OF WET COMBING AFTER RINSING NON-DETANGLING NEUTRALIZING SHAMPOO | 0.05837 | 0.00598 | 89.76 |
| 5TH COMBING: EASE OF DRY COMBING | 0.00901 | 0.00080 | 91.12 |

TABLE 1 shows that hair treated with the present invention exhibits a significant decrease of over 88% in combing work as compared to the Control hair treated as described in COMPARATIVE EXAMPLE I, below. The result of the decrease is less damage to the hair due to combing.

COMPARATIVE EXAMPLE I
CONTROL

A hair tress as described above in EXAMPLE I was treated as a control hair tress. The control tress was treated with 6 gm of Affirm® Sensitive Scalp Relaxer for 18 minutes, rinsed with water, shampooed using 1.0 ml of the non-detangling neutralizing shampoo, rinsed again and dried. Testing was done according to the schedule of EXAMPLE I, above. The test results are shown in TABLE 1, above.

The percent decrease in combing work was determined using the following formula:

$$100 \times (\text{work done}_{CT} - \text{work done}_{TT}) / \text{work done}_{CT} = \% \text{ decrease}$$

wherein work done$_{CT}$ is the combing work done for the control tress and work done$_{TT}$ is the combing work done for the test tress of the present composition. The precent decrease is provided in TABLE 1, above.

EXAMPLE II
SALON TEST OF PRECONDITIONER AND CONTROL

A salon test was conducted using five African-American subjects. Each subject's hair was parted down the middle to form left and right sections. On each subject, one section was treated with 5 gm of neat BETZ® polymer 1195, while the other section was not so treated. Both sections were then treated with the same amount of Affirm® Sensitive Scalp Relaxer for a time period of about 18 minutes or until the hair was essentially straight. Both sections were then rinsed with water, touched by hand to determine the hair's feel and combed by hand to subjectively test the ease of combing. Both sections were then shampooed using equal amounts of the non-detangling neutralizing shampoo, rinsed with water, touched to determine the hair's feel and combed by hand to subjectively test the ease of combing. The test results are provided in TABLE 2, below.

TABLE 2

Pre-Relaxer Conditioner with Betz ® Polymer 1195

5 HEADS:

| PROPERTIES | CONTROL | 1195 PRECON- DITIONER | NO DIFFER- ENCE | NOT RE- PORTED |
|---|---|---|---|---|
| EASE OF WET COMBING AFTER RINSING RELAXER: | | | | |
| •EQUAL | — | — | — | — |
| •BETTER | — | 5 | — | — |
| FEEL OF WET HAIR AFTER RINSING RELAXER: | | | | |
| •SOFTER | — | 5 | — | — |
| •SMOOTHER | — | 5 | — | — |
| •SILKIER | — | 1 | — | 4 |
| EASE OF WET COMBING AFTER RINSING NON- DETANGLING NEUTRALIZING SHAMPOO: | | | | |
| •EQUAL | — | — | — | — |
| •BETTER | — | 5 | — | — |
| FEEL OF WET HAIR AT COMPLETION: | | | | |
| •SOFTER | — | 5 | — | — |
| •SMOOTHER | — | 5 | — | — |
| •SILKIER | — | 1 | — | 4 |

TABLE 2 shows that, when reported, hair treated with the present invention has better ease of combing and is softer, smoother and silkier than the Control hair treated in accordance with COMPARATIVE EXAMPLE I, above.

The hair treated with the BETZ® polymer 1195 was easy to comb during the work stage and felt soft to the touch. Hair loss from the comb was minimal or negligible as compared to the control.

EXAMPLE III

BETZ® POLYMER 1195—CONTAINING PRECONDITIONER

A hair tress as described above in EXAMPLE I was treated and tested as described in EXAMPLE I except that 0.33 gm of a preconditioner having about 20 wt % BETZ® polymer 1195 and about 80 wt % glycerin was used as the preconditioner. The test results and a comparison with the Control of COMPARATIVE EXAMPLE I are provided in TABLE 3, below.

TABLE 3

Pre-Relaxer Conditioner with Betz ® Polymer 1195 & Glycerin

| PROPERTIES | CONTROL (JOULES) | 1195 - CONTAINING PRECONDITIONER (JOULES) | % DECREASE IN COMBING WORK |
|---|---|---|---|
| 1ST COMBING: INITIAL DETANGLING RIGHT AFTER RINSING RELAXER | 0.11380 | 0.01663 | 85.39 |
| 2ND COMBING: EASE OF WET COMBING AFTER RINSING RELAXER | 0.09200 | 0.01200 | 86.96 |
| 3RD COMBING: INITIAL DETANGLING RIGHT AFTER RINSING NON-DETANGLING NEUTRALIZING SHAMPOO | 0.09300 | 0.01008 | 89.16 |
| 4TH COMBING: EASE OF WET COMBING AFTER RINSING NON-DETANGLING NEUTRALIZING SHAMPOO | 0.05837 | 0.00939 | 83.91 |
| 5TH COMBING: EASE OF DRY COMBING | 0.00901 | 0.00294 | 67.37 |

TABLE 3 shows that hair treated with the present invention exhibits a significant average decrease of over 86% in wet combing work and over 67% in dry combing work as compared to the Control hair treated as described in COMPARATIVE EXAMPLE I, above. The result of the decrease is less damage to the hair due to combing.

A salon test as described above in EXAMPLE II was performed, except that the glycerin containing preconditioner was used in place of the neat BETZ® polymer 1195. The test results are provided in TABLE 4, below.

TABLE 4

Pre-Relaxer Conditioner with Betz ® Polymer 1195 & Glycerin

5 HEADS:

| PROPERTIES | CONTROL | 1195 - CONTAINING PRECONDITIONER | NO DIFFERENCE | NOT REPORTED |
|---|---|---|---|---|
| EASE OF WET COMBING AFTER RINSING RELAXER: | | | | |
| •EQUAL | — | — | — | — |
| •BETTER FEEL OF WET HAIR AFTER RINSING | — | 5 | — | — |
| RELAXER: | | | | |
| •SOFTER | — | 5 | — | — |
| •SMOOTHER | — | 5 | — | — |
| •SILKIER | — | 5 | — | — |
| EASE OF WET COMBING AFTER RINSING NON-DETANGLING NEUTRALIZING SHAMPOO: | | | | |
| •EQUAL | — | — | — | — |
| •BETTER FEEL OF WET HAIR AT COMPLETION: | — | 5 | — | — |
| •SOFTER | — | 5 | — | — |
| •SMOOTHER | — | 5 | — | — |
| •SILKIER | — | 5 | — | — |

TABLE 4 shows that hair treated with the present invention has better ease of combing and is softer, smoother and silkier than the Control hair treated in accordance with COMPARATIVE EXAMPLE I, above.

EXAMPLE IV

MULTI-PART RELAXER CONTAINING BETZ POLYMER 1195

A sensitive scalp multi-part relaxer, including creme relaxer (Part A) and liquid activator (Part B) was tested. The creme relaxer included 48.35 wt % deionized water, 2 wt % propylene glycol, 2.4 wt % BETZ® polymer 1195 (50% activity), 5.5 wt % calcium hydroxide, 2.25 wt % PEG-75 lanolin, 12 wt % petroleum jelly, 18 wt % mineral oil, 1.5 wt % Ceteth 20 (a cetyl alcohol with 20 moles of ethylene oxide commercially available from Lipo Chemicals, Peterson, N.J.) and 8 wt % stearyl alcohol. These components were introduced into a suitable vessel and mixed together to produce the creme relaxer. The liquid activator included 75 wt % deionized water and 25 wt % guanidine carbonate. The creme relaxer and the liquid activator were mixed at a 3.28:1, respectively, weight ratio to generate guanidine hydroxide in situ just prior to application to the hair tress.

A hair tress was treated and tested as described above in EXAMPLE I except that the relaxer of this example was used and the preconditioner was not used. The test results and a comparison with the Control are provided in TABLE 5, below.

TABLE 5

Sensitive Scalp Relaxer with Betz ® Polymer 1195

| PROPERTIES | CON-TROL (JOULES) | 1195 - CONTAINING MULTI-PART RELAXER (JOULES) | % DECREASE IN COMBING WORK |
|---|---|---|---|
| 1ST COMBING: INITIAL DETANGLING RIGHT AFTER RINSING RELAXER | 0.11380 | 0.02117 | 81.40 |
| 2ND COMBING: EASE OF WET COMBING AFTER RINSING RELAXER | 0.09200 | 0.02187 | 76.23 |
| 3RD COMBING: INITIAL DETANGLING RIGHT AFTER RINSING NON-DETANGLING NEUTRALIZING SHAMPOO | 0.09300 | 0.01301 | 86.01 |
| 4TH COMBING: EASE OF WET COMBING AFTER RINSING NON-DETANGLING NEUTRALIZING SHAMPOO | 0.05837 | 0.00819 | 85.97 |
| 5TH COMBING: EASE OF DRY COMBING | 0.00901 | 0.01200 | -33.19 |

TABLE 5 shows that hair treated with the present invention exhibits a significant average decrease of over 59% in combing work as compared to the Control hair treated as described in COMPARATIVE EXAMPLE I, above. The result of the decrease is less damage to the hair due to combing.

A salon test was also conducted as described above in EXAMPLE II using the above-described relaxer but without the preconditioner. The test results are provided in TABLE 6, below.

TABLE 6

Sensitive Scalp Relaxer with Betz ® Polymer 1195

5 HEADS:

| PROPERTIES | CON-TROL | 1195 - CONTAINING MULTI-PART RELAXER | NO DIFFER-ENCE | NOT REPORTED |
|---|---|---|---|---|
| EASE OF WET COMBING AFTER RINSING RELAXER: | | | | |
| •EQUAL | — | — | — | — |
| •BETTER | — | 5 | — | — |
| FEEL OF WET HAIR AFTER RINSING RELAXER: | | | | |
| •SOFTER | — | 5 | — | — |
| •SMOOTHER | — | 5 | — | — |
| •SILKIER | — | 5 | — | — |
| EASE OF WET COMBING AFTER RINSING NON-DETANGLING NEUTRALIZING SHAMPOO: | | | | |
| •EQUAL | — | — | — | — |
| •BETTER | — | 5 | — | — |
| FEEL OF WET HAIR AT COMPLETION: | | | | |
| •SOFTER | — | 5 | — | — |
| •SMOOTHER | — | 5 | — | — |
| •SILKIER | — | 5 | — | — |

TABLE 6 shows that hair treated with the present invention has better ease of combing and is softer, smoother and silkier than the Control hair treated in accordance with COMPARATIVE EXAMPLE I, above.

EXAMPLE V
BETZ® POLYMER 1195—CONTAINING SODIUM HYDROXIDE RELAXER

A BETZ® polymer 1195—containing sodium hydroxide no-base relaxer was tested on a hair tress. The sodium hydroxide relaxer included 53.28 wt % deionized water, 2 wt % propylene glycol, 2 wt % Betz polymer 1195 (50% activity), 0.49 wt % PEG-60 lanolin (polyethylene glycol commercially available from Croda Chemicals, Inc., New York, N.Y.), 0.98 wt % Laneth-15 (lanolin alcohol with 15 moles of ethylene oxide commercially available from Croda Chemicals, Inc., New York, N.Y.), 12 wt % petroleum jelly, 17 wt % mineral oil, 10 wt % emulsifying wax NF and 2.25 wt % sodium hydroxide. These components were introduced into a suitable vessel and mixed together to produce the relaxer.

A hair tress was treated and tested as described above in EXAMPLE I except that the relaxer of this example was used and the preconditioner was not used. The test results and a comparison with the Control are provided in TABLE 7, below.

TABLE 7

Sodium Hydroxide Relaxer with Betz ® Polymer 1195

| PROPERTIES | CON-TROL (JOULES) | 1195 - CONTAINING RELAXER (JOULES) | % DECREASE IN COMBING WORK |
|---|---|---|---|
| 1ST COMBING: INITIAL DETANGLING RIGHT AFTER RINSING RELAXER | 0.02933 | 0.00412 | 85.95 |
| 2ND COMBING: EASE OF WET COMBING AFTER RINSING RELAXER | 0.02297 | 0.00458 | 80.06 |
| 3RD COMBING: INITIAL DETANGLING RIGHT AFTER RINSING NON-DETANGLING NEUTRALIZING SHAMPOO | 0.01793 | 0.00240 | 86.61 |

TABLE 7-continued

Sodium Hydroxide Relaxer with Betz ® Polymer 1195

| PROPERTIES | CON-TROL (JOULES) | 1195 - CONTAINING RELAXER (JOULES) | % DECREASE IN COMBING WORK |
|---|---|---|---|
| 4TH COMBING: EASE OF WET COMBING AFTER RINSING NON-DETANGLING NEUTRALIZING SHAMPOO | 0.02273 | 0.00306 | 86.54 |
| 5TH COMBING: EASE OF DRY COMBING | 0.00093 | 0.00156 | −67.74 |

TABLE 7 shows that hair treated with the present invention exhibits a significant average decrease of over 54% in combing work as compared to the Control hair treated as described in COMPARATIVE EXAMPLE I, above. The result of the decrease is less damage to the hair due to combing.

A salon test was also conducted as described above in EXAMPLE II using the above-described relaxer but without the preconditioner. The test results are provided in TABLE 8, below.

TABLE 8

Sodium Hydroxide Relaxer with Betz ® Polymer 1195

5 HEADS:

| PROPERTIES | CON-TROL | 1195 - CONTAINING RELAXER | NO DIFFER-ENCE | NOT REPORTED |
|---|---|---|---|---|
| EASE OF WET COMBING AFTER RINSING RELAXER: | | | | |
| •EQUAL | — | — | — | — |
| •BETTER | — | 5 | — | — |
| FEEL OF WET HAIR AFTER RINSING RELAXER: | | | | |
| •SOFTER | — | 5 | — | — |
| •SMOOTHER | — | 4 | — | 1 |
| •SILKIER | — | 1 | — | 4 |
| EASE OF WET COMBING AFTER RINSING NON-DETANGLING NEUTRALIZING SHAMPOO: | | | | |
| •EQUAL | — | — | 1 | — |
| •BETTER | — | 4 | — | — |
| FEEL OF WET HAIR AT COMPLETION: | | | | |
| •SOFTER | — | 5 | — | — |
| •SMOOTHER | — | 4 | — | 1 |
| •SILKIER | — | 1 | — | 4 |

TABLE 8 shows that, when reported, hair treated with the present invention has better ease of combing and is softer, smoother and silkier than the Control hair treated in accordance with COMPARATIVE EXAMPLE I, above.

EXAMPLE VI

NEUTRALIZING SHAMPOO CONTAINING BETZ® POLYMER 1195

BETZ® polymer 1195 was incorporated into a neutralizing shampoo base that was previously formulated to bring the pH of the hair back to the normal range, i.e., 4.5 to 5.5, and make the relaxed hair easier to comb in the wet and dry stages.

The BETZ® polymer 1195 containing shampoo included 79.3 wt % deionized water, 0.2 wt % methylparaben, 0.1 wt % propylparaben, 0.35 wt % imidazolidinyl urea, 0.2 wt % disodium ethylenediaminetetraacetic acid, 1.6 wt % citric acid, 2 wt % Betz polymer 1195 (50% activity), 8 wt % cocoamphocarboxypropionate, 0.75 ammonium lauryl sulfate, 4 wt % cocoamide diethanolamine, 3 wt % polysorbate 20 and 0.5 wt % fragrance. These components were introduced into a suitable vessel and mixed together to produce the neutralizing shampoo.

A hair tress was treated and tested as described above in EXAMPLE I except without the preconditioner and the neutralizing shampoo was the BETZ® polymer 1195 containing neutralizing shampoo. The test results and a comparison with the Control are provided in TABLE 9, below.

TABLE 9

Neutralizing Shampoo with Betz ® Polymer 1195

| PROPERTIES | CON-TROL (JOULES) | SHAMPOO WITH 1195 (JOULES) | % DECREASE IN COMBING WORK |
|---|---|---|---|
| 1ST COMBING: INITIAL DETANGLING RIGHT AFTER RINSING RELAXER | 0.11380 | 0.03853 | 66.14 |
| 2ND COMBING: EASE OF WET COMBING AFTER RINSING RELAXER | 0.09200 | 0.05133 | 44.21 |
| 3RD COMBING: INITIAL DETANGLING RIGHT AFTER RINSING NON-DETANGLING NEUTRALIZING SHAMPOO | 0.09300 | 0.01530 | 83.55 |
| 4TH COMBING: EASE OF WET COMBING AFTER RINSING NON-DETANGLING NEUTRALIZING SHAMPOO | 0.05837 | 0.01500 | 74.30 |
| 5TH COMBING: EASE OF DRY COMBING | 0.00901 | 0.00735 | 18.42 |

TABLE 9 shows that hair treated with the present invention exhibits a significant average decrease of over 57% in combing work as compared to the Control hair treated as described in COMPARATIVE EXAMPLE I, above. The result of the decrease is less damage to the hair due to combing.

A salon test as described in EXAMPLE II was conducted with the neutralizing shampoo used for one side being the BETZ® polymer 1195 containing neutralizing shampoo but without the preconditioner. The test results are provided in TABLE 10, below.

TABLE 10

Neutralizing Shampoo with Betz ® Polymer 1195

5 HEADS:

| PROPERTIES | CONTROL | SHAMPOO WITH 1195 | NO DIFFERENCE | NOT REPORTED |
|---|---|---|---|---|
| EASE OF WET COMBING AFTER RINSING NEUTRALIZING SHAMPOO: | | | | |
| •EQUAL | — | — | 1 | — |
| •BETTER | — | 4 | — | — |
| FEEL OF WET HAIR AT COMPLETION: | | | | |
| •SOFTER | 1 | 3 | — | 1 |
| •SMOOTHER | — | 3 | — | 2 |
| •SILKIER | — | 1 | — | 4 |

TABLE 10 shows that the ease of wet combing for hair treated with the present invention was considered better by four out of five subject than the Control hair treated in accordance with COMPARATIVE EXAMPLE I, above. One subject reported that there was no difference. When reported, the feel of the wet hair treated with the present invention was softer, smoother and silkier with only one subject reporting that the Control hair treated in accordance with COMPARATIVE EXAMPLE I was softer.

EXAMPLE VII
USE OF PRECONDITIONER, SENSITIVE-SCALP, RELAXER AND NEUTRALIZING SHAMPOO ALL CONTAINING BETZ® POLYMER 1195

A hair tress as described in EXAMPLE I, above, was treated with a conditioning relaxer system including the preconditioner of EXAMPLE II, the relaxer of EXAMPLE IV and the neutralizing shampoo of EXAMPLE VI. Testing was conducted as described in EXAMPLE I. The test results and a comparison with the Control are provided in TABLE 11, below.

TABLE 11

Pre-Relaxer Conditioner, Sensitive Scalp Relaxer, and Neutralizing Shampoo, all with Betz ® Polymer 1195

| PROPERTIES | CONTROL (JOULES) | 1195 CONTAINING COMPOSITIONS (JOULES) | % DECREASE IN COMBING WORK |
|---|---|---|---|
| 1ST COMBING: INITIAL DETANGLING RIGHT AFTER RINSING RELAXER | 0.11380 | 0.02357 | 79.29 |
| 2ND COMBING: EASE OF WET COMBING AFTER RINSING RELAXER | 0.09200 | 0.01947 | 78.84 |
| 3RD COMBING: INITIAL DETANGLING RIGHT AFTER RINSING NON-DETANGLING NEUTRALIZING SHAMPOO | 0.09300 | 0.00853 | 90.83 |
| 4TH COMBING: EASE OF WET COMBING AFTER RINSING NON-DETANGLING NEUTRALIZING SHAMPOO | 0.05837 | 0.00927 | 84.12 |
| 5TH COMBING: EASE OF DRY COMBING | 0.00901 | 0.00665 | 26.19 |

TABLE 11 shows that hair treated with the present invention exhibits a significant average decrease of over 71% in combing work as compared to the Control hair treated as described in COMPARATIVE EXAMPLE I, above. The result of the decrease is less damage to the hair due to combing.

A salon test as described above in EXAMPLE II was conducted but using the above-described BETZ® polymer 1195 containing compositions. The test results are provided in TABLE 12, below.

TABLE 12

Pre-Relaxer Conditioner, Sensitive Scalp Relaxer, and Neutralizing Shampoo, all with Betz ® Polymer 1195

| PROPERTIES | CONTROL | 1195 CONTAINING COMPOSITIONS | NO DIFFERENCE | NOT REPORTED |
|---|---|---|---|---|
| EASE OF WET COMBING AFTER RINSING RELAXER: | | | | |
| •EQUAL | — | — | — | — |
| •BETTER | — | 5 | — | — |
| FEEL OF WET HAIR AFTER RINSING RELAXER: | | | | |
| •SOFTER | — | 5 | — | 2 |
| •SMOOTHER | — | 4 | — | 3 |
| •SILKIER | — | 3 | — | 3 |
| EASE OF WET COMBING AFTER RINSING NON-DETANGLING NEUTRALIZING SHAMPOO: | | | | |
| •EQUAL | — | — | — | — |
| •BETTER | — | 5 | — | — |
| FEEL OF WET HAIR AT COMPLETION: | | | | |
| •SOFTER | — | 5 | — | — |
| •SMOOTHER | — | 5 | — | — |
| •SILKIER | — | 4 | — | 1 |

TABLE 12 shows that, when reported, hair treated with the present invention has better ease of combing and is softer, smoother and silkier than the Control hair treated in accordance with COMPARATIVE EXAMPLE I, above.

FIG. 2 is a graph of the combing load (gm) vs. distance from the top of the hair tress 30, in centimeters (cm), for both the Control hair tress of COMPARATIVE EXAMPLE I and a hair tress treated with the conditioning relaxer system of this example.

FIG. 3 is a bar graph comparing the percent work required to comb the Control hair tress versus a hair tress treated with the conditioning relaxer system of this example.

EXAMPLE VIII

SALCARE SC95 CONTAINING RELAXER

A sensitive scalp multi-part relaxer, including creme relaxer (Part A) and liquid activator (Part B) was tested. The composition of the creme relaxer is described in EXAMPLE IV, above, with the exception that Salcare SC95, commercially available from Allied Colloids, Suffolk, Va. was substituted for the BETZ® polymer 1195. The liquid activator is also disclosed in EXAMPLE IV.

A hair tress was treated and tested as described above in EXAMPLE I except the relaxer of this example was used and the preconditioner was not used. The test results and a comparison with the Control are provided in TABLE 13, below.

TABLE 13

Sensitive Scalp Relaxer with Salcare SC95

| PROPERTIES | CONTROL (JOULES) | SALCARE SC95 CONTAINING RELAXER (JOULES) | % DECREASE IN COMBING WORK |
|---|---|---|---|
| 1ST COMBING: INITIAL DETANGLING RIGHT AFTER RINSING RELAXER | 0.11380 | 0.02057 | 81.92 |
| 2ND COMBING: EASE OF WET COMBING AFTER RINSING RELAXER | 0.09200 | 0.01810 | 80.33 |
| 3RD COMBING: INITIAL DETANGLING RIGHT AFTER RINSING NON-DETANGLING NEUTRALIZING SHAMPOO | 0.09300 | 0.01297 | 86.05 |
| 4TH COMBING: EASE OF WET COMBING AFTER RINSING NON-DETANGLING NEUTRALIZING SHAMPOO | 0.05837 | 0.00938 | 83.95 |
| 5TH COMBING: EASE OF DRY COMBING | 0.00901 | 0.00919 | −1.99 |

TABLE 13 shows that hair treated with the present invention exhibits a significant average decrease of over 66% in combing work as compared to the Control hair treated as described in COMPARATIVE EXAMPLE I, above. The result of the decrease is less damage to the hair due to combing.

A salon test was also conducted as described above in EXAMPLE II using the above-describe relaxer but without the preconditioner. The test results are provided in TABLE 14, below.

TABLE 14

Sensitive Scalp Relaxer with Salcare SC95

| PROPERTIES | CONTROL | SC95 CONTAINING RELAXER | NO DIFFERENCE | NOT REPORTED |
|---|---|---|---|---|
| EASE OF WET COMBING AFTER RINSING RELAXER: | | | | |
| •EQUAL | — | — | — | — |
| •BETTER | — | 5 | — | — |
| FEEL OF WET HAIR AFTER RINSING RELAXER: | | | | |
| •SOFTER | — | 3 | — | 2 |
| •SMOOTHER | — | 3 | — | 2 |
| •SILKIER | — | 4 | — | 1 |
| EASE OF WET COMBING AFTER RINSING NON-DETANGLING NEUTRALIZING SHAMPOO: | | | | |
| •EQUAL | — | — | — | — |
| •BETTER | — | 5 | — | — |
| FEEL OF WET HAIR AT COMPLETION: | | | | |
| •SOFTER | — | 3 | — | 2 |
| •SMOOTHER | — | 3 | — | 2 |
| •SILKIER | — | 4 | — | 1 |

TABLE 14 shows that, when reported, hair treated with the present invention has better ease of combing and is softer, smoother and silkier than the Control hair treated in accordance with COMPARATIVE EXAMPLE I, above.

EXAMPLE IX

NEUTRALIZING SHAMPOO CONTAINING SALCARE SC95

Salcare SC95 was incorporated into a neutralizing shampoo base. The Salcare SC95 containing shampoo was similar to the BETZ® polymer 1195 containing neutralizing shampoo described in EXAMPLE VI, above, except that the Salcare SC95 was substituted for the BETZ® polymer 1195.

A hair tress was treated and tested as described above in EXAMPLE I except that a preconditioner was not used and the neutralizing shampoo was the Salcare SC95 containing neutralizing shampoo. The test results and a comparison with the Control are provide in TABLE 15, below.

TABLE 15

Neutralizing Shampoo with Salcare SC95

| PROPERTIES | CONTROL (JOULES) | SC95 - CONTAINING SHAMPOO (JOULES) | % DECREASE IN COMBING WORK |
|---|---|---|---|
| 1ST COMBING: INITIAL DETANGLING RIGHT AFTER RINSING RELAXER | 0.11380 | 0.09815 | 13.75 |

TABLE 15-continued

Neutralizing Shampoo with Salcare SC95

| PROPERTIES | CONTROL (JOULES) | SC95 - CONTAINING SHAMPOO (JOULES) | % DECREASE IN COMBING WORK |
|---|---|---|---|
| 2ND COMBING: EASE OF WET COMBING AFTER RINSING RELAXER | 0.09200 | 0.07240 | 21.30 |
| 3RD COMBING: INITIAL DETANGLING RIGHT AFTER RINSING NON-DETANGLING NEUTRALIZING SHAMPOO | 0.09300 | 0.01843 | 80.18 |
| 4TH COMBING: EASE OF WET COMBING AFTER RINSING NON-DETANGLING NEUTRALIZING SHAMPOO | 0.05837 | 0.01447 | 75.21 |
| 5TH COMBING: EASE OF DRY COMBING | 0.00901 | 0.00303 | 66.37 |

TABLE 15 shows that hair treated with the present invention exhibits a significant average decrease of over 51% in combing work as compared to the Control hair treated as described in COMPARATIVE EXAMPLE I, above. The result of the decrease is less damage to the hair due to combing.

A salon test as described in EXAMPLE II was conducted but the neutralizing shampoo used for the one side was the Salcare SC95 containing neutralizing

TABLE 16

Neutralizing Shampoo with Salcare SC95

5 HEADS:

| PROPERTIES | CONTROL | SC95 - CONTAINING SHAMPOO | NO DIFFERENCE | NOT REPORTED |
|---|---|---|---|---|
| EASE OF WET COMBING AFTER RINSING NEUTRALIZING SHAMPOO: | | | | |
| •EQUAL | — | — | — | — |
| •BETTER | — | 5 | — | — |
| FEEL OF WET HAIR AT COMPLETION: | | | | |
| •SOFTER | — | 4 | — | 1 |
| •SMOOTHER | — | 4 | — | 1 |
| •SILKIER | — | 1 | — | 4 |

TABLE 16 shows that, when reported, hair treated with the present invention has better ease of combing and is softer, smoother and silkier than the Control hair treated in accordance with COMPARATIVE EXAMPLE I, above.

EXAMPLE X
MULTI-PART RELAXER CONTAINING JR-30M

A sensitive scalp multi-part relaxer, including creme relaxer (Part A) and liquid activator (Part B) was tested. The composition of the creme relaxer is disclosed in EXAMPLE IV, above, except that 1.2 wt % of JR-30M, commercially available from Amerchol Corp., Addison, N.J. was used in place of the BETZ® polymer 1195 and 49.55 wt % of deionized water was used. The liquid activator had the composition disclosed in EXAMPLE IV.

A hair tress was treated and tested as described above in EXAMPLE I except that the preconditioner was not used and the relaxer used was the above-identified SC95 containing relaxer. The test results and a comparison with the Control, are provided in TABLE 17, below.

TABLE 17

Sensitive Scalp Relaxer with UCare Polymer JR-30M

| PROPERTIES | CONTROL (JOULES) | JR-30M- CONTAINING RELAXER (JOULES) | % DECREASE IN COMBING WORK |
|---|---|---|---|
| 1ST COMBING: INITIAL DETANGLING RIGHT AFTER RINSING RELAXER | 0.11380 | 0.01400 | 87.70 |
| 2ND COMBING: EASE OF WET COMBING AFTER RINSING RELAXER | 0.09200 | 0.00955 | 89.62 |
| 3RD COMBING: INITIAL DETANGLING RIGHT AFTER RINSING NON-DETANGLING NEUTRALIZING SHAMPOO | 0.09300 | 0.02153 | 76.85 |
| 4TH COMBING: EASE OF WET COMBING AFTER RINSING NON-DETANGLING NEUTRALIZING SHAMPOO | 0.05837 | 0.01480 | 74.64 |
| 5TH COMBING: EASE OF DRY COMBING | 0.00901 | 0.00524 | 41.84 |

TABLE 17 shows that hair treated with the present invention exhibits a significant average decrease of over 74% in combing work as compared to the Control hair treated as described in COMPARATIVE EXAMPLE I, above. The result of the decrease is less damage to the hair due to combing.

A salon test was also conducted as described above in EXAMPLE II using the SC-95 relaxer but the preconditioner was not used. The test results are provided in TABLE 18, below.

TABLE 18

Sensitive Scalp Relaxer with UCare Polymer JR-30M

5 HEADS:

| PROPERTIES | CONTROL | JR-30M - CONTAINING RELAXER | NO DIFFERENCE | NOT REPORTED |
|---|---|---|---|---|
| EASE OF WET COMBING AFTER RINSING RELAXER: | | | | |
| •EQUAL | — | — | — | — |
| •BETTER | — | 5 | — | — |
| FEEL OF WET HAIR AFTER RINSING RELAXER: | | | | |
| •SOFTER | — | 4 | — | 1 |
| •SMOOTHER | — | 3 | — | 2 |

TABLE 18-continued

Sensitive Scalp Relaxer with UCare Polymer JR-30M

5 HEADS:

| PROPERTIES | CONTROL | JR-30M - CONTAINING RELAXER | NO DIFFERENCE | NOT REPORTED |
|---|---|---|---|---|
| •SILKIER | — | 2 | — | 3 |
| EASE OF WET COMBING AFTER RINSING NON-DETANGLING NEUTRALIZING SHAMPOO: | | | | |
| •EQUAL | — | — | — | — |
| •BETTER FEEL OF WET HAIR AT COMPLETION: | — | 5 | — | — |
| •SOFTER | — | 4 | — | 1 |
| •SMOOTHER | — | 3 | — | 2 |
| •SILKIER | — | 2 | — | 3 |

TABLE 18 shows that, when reported, hair treated with the present invention has better ease of combing and is softer, smoother and silkier than the Control hair treated in accordance with COMPARATIVE EXAMPLE I, above.

EXAMPLE XI
JR-30M CONTAINING SODIUM HYDROXIDE RELAXER

A JR-30M containing sodium hydroxide no base relaxer including 52.25 wt % deionized water, 2 wt % propylene glycol, 1 wt % JR-30M, 0.5 wt % PEG-60 lanolin, 1 wt % Laneth-15, 12 wt % petroleum jelly, 18 wt % mineral oil, 10 wt % emulsifying wax NF, 1 wt % cetyl alcohol and 2.25 wt % sodium hydroxide, was tested on a hair tress described above in EXAMPLE I. The tress was treated and tested as described in EXAMPLE I except the relaxer was the above-identified relaxer and no preconditioner was used. The test results and a comparison with the Control are provided in TABLE 19, below.

TABLE 19

Sodium Hydroxide Relaxer with UCare Polymer JR-30M

| PROPERTIES | CONTROL (JOULES) | JR-30M-CONTAINING RELAXER (JOULES) | % DECREASE IN COMBING WORK |
|---|---|---|---|
| 1ST COMBING: INITIAL DETANGLING RIGHT AFTER RINSING RELAXER | 0.02933 | 0.00478 | 83.70 |
| 2ND COMBING: EASE OF WET COMBING AFTER RINSING RELAXER | 0.02297 | 0.00441 | 78.62 |
| 3RD COMBING: INITIAL DETANGLING RIGHT AFTER RINSING NON-DETANGLING NEUTRALIZING SHAMPOO | 0.01793 | 0.00491 | 72.62 |
| 4TH COMBING: EASE OF WET COMBING AFTER RINSING NON-DETANGLING | 0.02273 | 0.00447 | 80.33 |
| NEUTRALIZING SHAMPOO 5TH COMBING: EASE OF DRY COMBING | 0.00093 | 0.00311 | −234.41 |

TABLE 19 shows that hair treated with the present invention exhibits a significant decrease of over 70% in combing work for the first four combings as compared to the Control hair treated in accordance with COMPARATIVE EXAMPLE I, above.

A salon test was also conducted as described above in EXAMPLE II using the above-identified relaxer but the preconditioner was not used. The test results are provided in TABLE 20, below.

TABLE 20

Sodium Hydroxide Relaxer with UCare Polymer JR-30M

5 HEADS:

| PROPERTIES | CONTROL | JR-30M - CONTAINING RELAXER | NO DIFFERENCE | NOT REPORTED |
|---|---|---|---|---|
| EASE OF WET COMBING AFTER RINSING RELAXER: | | | | |
| •EQUAL | — | — | — | — |
| •BETTER FEEL OF WET HAIR AFTER RINSING RELAXER: | — | 5 | — | — |
| •SOFTER | — | 3 | — | 2 |
| •SMOOTHER | — | 2 | — | 3 |
| •SILKIER | — | — | — | 5 |
| EASE OF WET COMBING AFTER RINSING NON-DETANGLING NEUTRALIZING SHAMPOO: | | | | |
| •EQUAL | — | — | — | — |
| •BETTER FEEL OF WET HAIR AT COMPLETION: | — | 5 | — | — |
| •SOFTER | — | 3 | — | 2 |
| •SMOOTHER | — | 2 | — | 3 |
| •SILKIER | — | — | — | 5 |

TABLE 20 shows that, when reported, hair treated with the present invention has better ease of combing and is softer, smoother and silkier than the Control hair treated in accordance with COMPARATIVE EXAMPLE I, above.

EXAMPLE XII
SALCARE SC92 CONTAINING PRECONDITIONER

A hair tress as described above in EXAMPLE I was treated with neat Salcare SC92 commercially available from Allied Colloids, Suffolk, Va. as the preconditioner. The hair tress was treated and tested as described in EXAMPLE I. The test results and a comparison with the Control are provided in TABLE 21, below.

TABLE 21

Pre-Relaxer Conditioner with Salcare SC92

| PROPERTIES | CONTROL (JOULES) | SC92 - CONTAINING PRECONDITIONER (JOULES) | % DECREASE IN COMBING WORK |
|---|---|---|---|
| 1ST COMBING: INITIAL DETANGLING RIGHT AFTER RINSING RELAXER | 0.11380 | 0.01857 | 83.68 |
| 2ND COMBING: EASE OF WET COMBING AFTER RINSING RELAXER | 0.09200 | 0.01343 | 85.40 |
| 3RD COMBING: INITIAL DETANGLING RIGHT AFTER RINSING NON-DETANGLING NEUTRALIZING SHAMPOO | 0.09300 | 0.01195 | 87.15 |
| 4TH COMBING: EASE OF WET COMBING AFTER RINSING NON-DETANGLING NEUTRALIZING SHAMPOO | 0.05837 | 0.00857 | 85.32 |
| 5TH COMBING: EASE OF DRY COMBING | 0.00901 | 0.00427 | 52.61 |

TABLE 21 shows that hair treated with the present invention exhibits a significant average decrease of over 78% in combing work as compared to the Control hair treated as described in COMPARATIVE EXAMPLE I, above. The result of the decrease is less damage to the hair due to combing.

A salon test as described above in EXAMPLE II was performed, except that the neat Salcare SC92 was used as the preconditioner in place of the neat Betz polymer 1195. The test results are provided in TABLE 22, below.

TABLE 22

Pre-Relaxer Conditioner with Salcare SC92

5 HEADS:

| PROPERTIES | CONTROL | SALCARE SC92 - CONTAINING PRECONDITIONER | NO DIFFERENCE | NOT REPORTED |
|---|---|---|---|---|
| EASE OF WET COMBING AFTER RINSING RELAXER: | | | | |
| •EQUAL | — | — | — | — |
| •BETTER FEEL OF WET HAIR AFTER RINSING RELAXER: | — | 5 | — | — |
| •SOFTER | — | 5 | — | — |
| •SMOOTHER | — | 5 | — | 4 |
| •SILKIER | — | 1 | — | 4 |
| EASE OF WET COMBING AFTER RINSING NON-DETANGLING NEUTRALIZING SHAMPOO: | | | | |
| •EQUAL | — | — | — | — |
| •BETTER FEEL OF WET HAIR AT COMPLETION: | — | 5 | — | — |
| •SOFTER | — | 5 | — | — |
| •SMOOTHER | — | 1 | — | 4 |
| •SILKIER | — | 1 | — | 4 |

TABLE 22 shows that, when reported, hair treated with the present invention has better ease of combing and is softer, smoother and silkier than the Control hair treated in accordance with COMPARATIVE EXAMPLE I, above.

These polymers are stable in highly alkaline pH and they deposit on the hair fiber surfaces, thereby making the hair smooth, silky, and very easy to comb, at least during wet combing.

The invention is particularly well suited for decreasing combing damage to hair, especially hair that is subjected to a cosmetic procedure.

All patents, articles and the like referred to or otherwise identified in this specification are incorporated herein by reference in their entirety.

What is claimed is:

1. A hair relaxer composition that decreases combine damage due to relaxation of hair in at least two components comprising:
    (a) a first component containing an aqueous relaxer cream base comprising an alkaline hydroxide of an earth metal cation in combination with a water-dispersible cationic polymer admixture comprising the polymer dimethylaminoethylmethacrylate, mineral oil and PPG-1 trideceth 6 wherein the polymer is present in a concentration of from about 0.5% to about 3%; and
    (b) a second component containing an activator comprising an aqueous solution of a water-soluble organic salt of an organic base, the salt having an anion capable of being precipitated by the alkaline earth metal cation of the first component under a range of alkaline conditions from pH 11 to pH 13.5;
    whereby for use the first and second components are admixed to produce a hair relaxer composition which decreases combing damage to hair.

2. The hair relaxer composition of claim 11 wherein the alkaline hydroxide in the first component is calcium hydroxide and wherein the organic salt in the second component is guanidine carbonate.

3. The hair relaxer composition of claim 2 wherein the first component further comprises at least one polyol selected from the group consisting of glycerin and lower alkylene glycols with 2–5 carbon atoms per alkyl group.

4. A shampoo composition for decreasing combing damage to relaxed hair comprising a shampoo base said base comprising methylparaben, propylparaben, imidazolidinyl urea, disodium ethylenediaminetetraacetic acid, citric acid, cocamphocarboxypropionate, ammonium lauryl sulfate, cocamide diethanolamine, polysorbate 20 and fragrance and a water-soluble cationic polymer, wherein the polymer is dimethylaminoethylmethacrylate and the polymer is present in a range of 0.1 to 3% of the total weight of the shampoo composition.

5. A method for relaxing and decreasing combing damage to hair comprising the steps of:

(a) applying to the hair dimethylaminoethylmethacrylate in an amount effective to decrease combing damage to hair; then (b) applying to the hair a hair a relaxer composition which decreases combing damage due to relaxation of hair comprising an effective amount of a water-dispersible cationic polymer admixture comprising dimethylaminoethylmethacrylate, mineral oil and PPG-1 trideceth 6 wherein the polymer is present in a concentration of from about 0.5% to about 3%; and an effective amount of an alkaline hydroxide relaxing component for a time sufficient to at least partially relax the hair;

(c) rinsing at least a portion of the relaxing composition from the hair with water;

(d) then applying to the hair a shampoo composition for decreasing combing damage to relaxed hair for a time sufficient to neutralize the relaxed hair and remove at least a portion of the relaxing composition from the hair, wherein the shampoo composition comprises a shampoo base and dimethylaminoethylmethacrylate, wherein the dimethylaminoethylmethacrylate is present in a range of 0.1 to 3% of the total weight of the shampoo composition;

(e) rinsing substantially all of the shampoo composition from the hair with water.

6. The method of claim 5 wherein the hair relaxing composition comprises an effective amount of dimethylaminoethylmethacrylate and an effective amount of an alkaline hydroxide relaxing component and a polyol selected from the group consisting of glycerin or lower alkylene glycols with 2–5 carbon atoms per alkyl group, and wherein the dimethylaminoethylmethacrylate is present in a range of 0.5–3% of the total weight of the composition; and wherein the hydroxide relaxing component is sodium hydroxide.

7. The method of claim 5 wherein the hair relaxer composition comprises at least two components comprising:

(a) a first component containing an aqueous relaxer cream base comprising an alkaline hydroxide of an earth metal cation, in combination with dimethylaminoethylmethacrylate in a concentration of from about 0.5% to 3% of the total first component; and (b) a second component containing an activator comprising an aqueous solution of a water-soluble organic salt of an organic base, the salt having an anion capable of being precipitated by the alkaline earth metal cation of the first component under a range of alkaline conditions from pH 11 to pH 13.5, and wherein the salt comprises guanidine carbonate; and whereby for use the first and second components are admixed to produce a hair relaxer composition which decreases combing damage to hair.

8. The method of claim 5 wherein the dimethylaminoethylmethacrylate is admixed with at least one polyol selected from the group consisting of glycerin or lower alkylene glycols with 2–5 carbon atoms or alkyl group.

* * * * *